(12) United States Patent
Colvin

(10) Patent No.: US 8,594,807 B2
(45) Date of Patent: Nov. 26, 2013

(54) COMPLIANT STIMULATING ELECTRODES AND LEADS AND METHODS OF MANUFACTURE AND USE

(75) Inventor: Michael Steven Colvin, Malibu, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1683 days.

(21) Appl. No.: 11/120,526

(22) Filed: May 2, 2005

(65) Prior Publication Data

US 2006/0247749 A1 Nov. 2, 2006

(51) Int. Cl.
*A61N 1/05* (2006.01)

(52) U.S. Cl.
USPC .......................................... 607/117

(58) Field of Classification Search
USPC ................................ 607/116–117
See application file for complete search history.

(56) References Cited

U.S. PATENT DOCUMENTS

| 4,768,523 | A | * | 9/1988 | Cahalan et al. | 607/116 |
| 5,121,754 | A | * | 6/1992 | Mullett | 607/117 |
| 5,658,327 | A | * | 8/1997 | Altman et al. | 607/127 |
| 6,001,094 | A | | 12/1999 | Edwards et al. | |
| 6,516,227 | B1 | | 2/2003 | Meadows et al. | |
| 6,609,029 | B1 | | 8/2003 | Mann et al. | |
| 6,741,892 | B1 | | 5/2004 | Meadows et al. | |

FOREIGN PATENT DOCUMENTS

WO WO 97/10784 * 3/1997

OTHER PUBLICATIONS

U.S. Appl. No. 11/030,546, Paul M. Meadows.

* cited by examiner

*Primary Examiner* — Eric D. Bertram
(74) *Attorney, Agent, or Firm* — Frommer Lawrence & Haug LLP; Bruce E. Black

(57) ABSTRACT

A device for stimulating body tissue includes a lead body and at least one stimulating electrode disposed on the lead body. The lead body is configured and arranged to be substantially rigid outside the patient's body and during insertion into the patient's body and then becomes non-rigid upon exposure within the patient's body.

3 Claims, 3 Drawing Sheets

COMPLIANT STIMULATING ELECTRODES AND LEADS AND METHODS OF MANUFACTURE AND USE

FIELD

The invention is directed to electrodes and leads for stimulation and methods of manufacturing and using the electrodes and leads. In addition, the invention is directed to compliant electrodes and leads for stimulation and methods of manufacturing and using the electrodes and leads.

BACKGROUND

Electrical stimulation of body tissues can be used to treatment many different conditions and ailments, as well as treating pain. Many body tissues can be stimulated including, but not limited to, muscle and neural tissues. A lead with one or more stimulating electrodes is often inserted into the body to position the electrode(s) near the tissue to be stimulated. In many instances, a stylet, such as a metallic wire, is inserted into a lumen running through the center of the lead from the proximal end to the distal end to aid in insertion of the lead into the body. The stylet gives the lead rigidity during positioning and anchoring the lead in the body. Once the lead is positioned, the stylet can be removed and the lead then becomes flaccid.

The use of a stylet can have several limitations. A stylet can complicate and lengthen surgery. The stylet may perforate the lead assembly and may damage the lead or body tissues. The need for accommodating the stylet and the presence of the lumen for the stylet can complicate the manufacture of the lead. In addition, accommodating the stylet can also increase the overall diameter of the lead.

BRIEF SUMMARY

One embodiment is a device for stimulating tissue inside a patient's body. The device includes a lead body and at least one stimulating electrode disposed on the lead body. The lead body is configured and arranged to be substantially rigid outside the patient's body and during insertion into the patient's body and then becomes non-rigid upon exposure within the patient's body.

Another embodiment is a method of treating body tissue. A lead is inserted into the body tissue. The lead includes at least one stimulation electrode and a lead body. The lead body is rigid prior to and during insertion. The lead body becomes non-rigid after insertion and upon exposure to the body tissue. The body tissue is stimulated using the stimulation electrode.

Yet another embodiment is a device for stimulating tissue inside a patient's body. The device includes a lead body that is configured and arranged to be substantially rigid outside the patient's body and during insertion into the patient's body; at least one stimulating electrode disposed on the lead body; and means for making the lead body non-rigid after insertion into and exposure to the patient's body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to electrodes and leads for stimulation and methods of manufacturing and using the electrodes and leads. In addition, the present invention is directed to compliant electrodes and leads for stimulation and methods of manufacturing and using the electrodes and leads.

A lead arrangement can be made compliant by selecting material(s) for the lead body that allow the lead to be rigid outside of the patient's body and during insertion into the body and then become non-rigid or flaccid after insertion and exposure to the patient's body. The rigidity of the lead can be modified due to, for example, the temperature of the patient's body or the presence of water in the patient's body.

Figure 1:
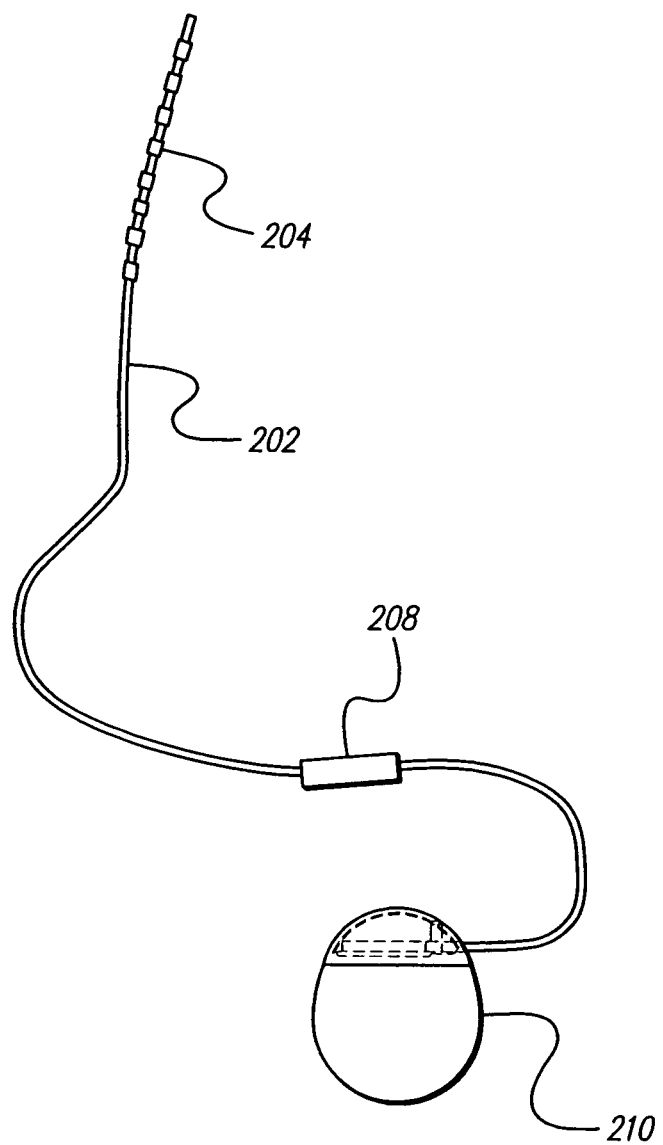
FIG. 1 is a schematic side view of one embodiment of a lead.

FIG. 1 illustrates one embodiment of a stimulation system. The stimulation system includes a lead 202, one or more stimulation electrodes 204 placed on the lead, a connector 208 for connection of the electrodes to a control unit 210, and a stylet (not shown) for assisting in insertion and positioning of the lead in the patient's tissue. Examples of suitable control units and lead connectors include those described in U.S. Pat. Nos. 6,516,227, 6,609,029, and 6,741,892, all of which are incorporated herein by reference, as well as the Precision™ Spinal Cord Stimulation System available from Advanced Bionics Corporation, Sylmar, Calif. and other commercially available stimulator units.

Figure 2:
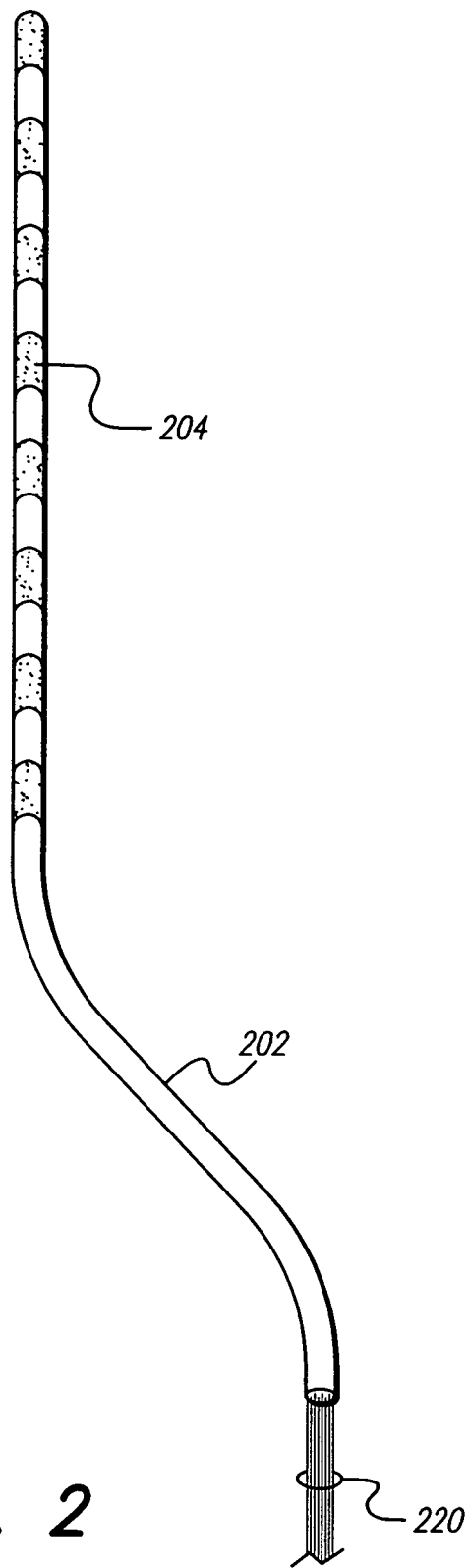
FIG. 2 is a schematic view of the distal end of the lead of FIG. 1.

FIG. 2 illustrates a view of the distal portion of the lead 202 having at least one electrode 204. Conductor or conductor wires 220 run through the lead body of the lead 202. A conductor wire 220 is electrically connected to at least one electrode 204. In some embodiments of the lead 202, a lumen (not shown) may run longitudinally within the lead 202, with the lumen having an opening at the proximal end of the lead. A stylet (not shown) may be inserted through the proximal opening and into the lumen before implantation of the lead. The stylet within the lead lumen helps stiffen the lead which is often too compliant for lead implantation, but which lead compliance is desired once the lead is implanted in body tissue. The stylet is not implanted but is withdrawn after the lead is implanted into the desired location inside the body tissue. In the illustrated embodiment, the lead is implanted near the spinal cord to stimulate the spinal cord. It will be understood, however, that other implantable leads useful for other applications are also included within the invention.

Figure 3:
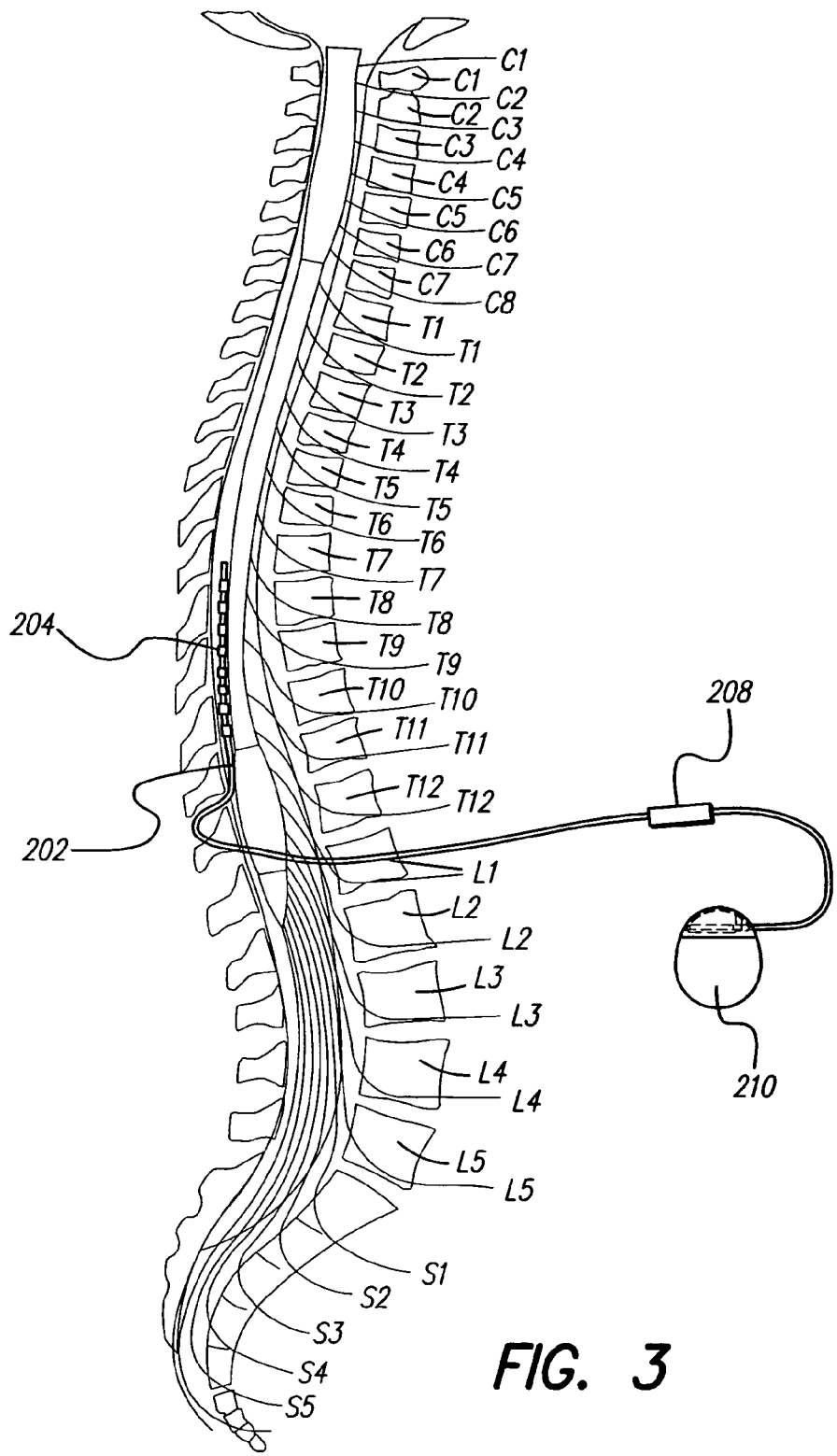
FIG. 3 is a schematic side view of one embodiment of a lead implanted along the spinal cord.

FIG. 3 schematically illustrates one embodiment of a stimulation system 200 that can be inserted into a patient's body without a stylet. The stimulation system can include a lead 202 having one or more stimulation electrodes 204, and an optional connector 208 for connection of the electrodes to a control unit. In at least some embodiments, the body of the lead 202 is solid (i.e., the lead does not include a lumen through the center of the lead.)

In accordance with the invention, the lead 202 can be formed of a non-conducting material and is rigid when it is outside the patient's body and during insertion and then becomes non-rigid or compliant upon extended exposure inside the patient's body. The transition time from a rigid state to a non-rigid or compliant state should be sufficient to allow a physician to implant, position, and anchor the lead. This time period may vary depending on the application. Suitable applications for the lead 202 include, but are not limited to, brain stimulation including deep brain stimulation, and spinal cord stimulation. In one embodiment, the lead 202 is made of a plastic material that has a glass transition temperature ($T_g$) that is near or less than body temperature. Preferably, the glass transition temperature is greater than room temperature, but in some embodiments the glass transition temperature can be less than or equal to room temperature and the lead can be stored in a sufficiently cold environment until it is needed for insertion. In one embodiment, the glass transition temperature of the plastic material of the lead is in the range of 25 to 38° C.

This plastic material typically includes a polymer which can be a homopolymer, a copolymer formed using two or more different monomeric units, or a mixture of polymers. The plastic material can also include additives such as filler, colorants, anti-oxidants, and the like. In particular, plasticizer additive(s) can be particularly useful to modify the glass transition temperature of the base polymer or mixture of polymers.

The selection of a suitable glass transition temperature and plastic material can be based on one of more factors including, but not limited to, biocompatibility, cost, ease of manufacture, stability, glass transition temperature of the plastic material, heat capacity of the plastic material, thermal mass of the lead, type of tissue to be stimulated, the depth of the tissue to be stimulated, thickness of the lead, flexibility of the lead material, and the like. For example, the selection of glass transition temperature may depend on the heat capacity of the plastic material and thermal mass of the lead. The lead should remain sufficiently rigid during insertion of the lead into the body to allow the lead to be positioned without becoming too flexible or non-rigid. The rapidity with which the lead increases temperature will be determined, at least in part, by the heat capacity and thermal mass of the lead. Thus, a lead with a relatively low glass transition temperature, low heat capacity, and small thermal mass will typically become non-rigid prior to a lead with higher glass transition temperature, higher heat capacity, and larger thermal mass. In some embodiments, the lead may be kept at a temperature below room temperature prior to insertion to maintain rigidity over a longer period of time before and after insertion.

In another embodiment, the lead 202 can be made of a plastic material that is initially rigid but becomes non-rigid as water or other body fluids are absorbed by the plastic material. One example of such a material is a crosslinked hydrogel. Hydrophobic polymers (e.g., silicone copolymers or polymers containing mainly aliphatic/aromatic backbones) that imbibe lipids (e.g., fats and cerebrosides) could also be used. The imbibed lipids can act as plasticizers and cause the polymer to soften. In one embodiment, a lead is assembled using a dehydrated crosslinked hydrogel that provides sufficient rigidity. After insertion of the lead into the body tissue, e.g., along and within the spinal cord, the hydrogel will absorb water from the tissues and body fluids and become non-rigid. The absorption rate of water by the hydrogel can be selected to provide sufficient time for the insertion of the lead into the tissue before the lead becomes too non-rigid for accurate insertion. The level of crosslinking of the hydrogel will often determine, at least in part, the ultimate softness of the lead after the absorption of water. Typically, the greater the degree of cross-linking, the firmer the lead will be. The degree of cross-linking may also impact the rate of absorption of water by the hydrogel.

In yet another embodiment, the lead 202 can include a soluble material that is soluble in body fluids, such as water, in combination with a relatively flexible or soft plastic material. The soluble material provides the rigidity for the lead. As the soluble material dissolves into the body fluids, the lead loses its rigidity. Examples of suitable soluble materials include sugars, anti-inflammatory agents, antibiotics, steroids or other medication, and the like. As above, the lead could contain a material soluble in body lipids or plasma proteins such as growth hormone, inflammatory agents, antibiotics, steroids or other medication. As these materials are released the lead becomes flaccid. As examples of combining the soluble material and the flexible or soft plastic material, the soluble material can be impregnated into the plastic material or the soluble material may be present as a coating on the outside of the lead, or the soluble material can be disposed within one or more spaces (e.g., lumens, gaps, interstices, clefts, pockets, hollows, fissures, and the like) within the lead. The solubility of the soluble material and the disposition of the soluble material within the lead can be selected to provide sufficient time for the lead to be inserted into the tissue before the lead becomes too non-rigid for accurate insertion. In some embodiments, the soluble material includes a drug or other compound for treatment of the tissue to be stimulated or other tissue.

In any of these embodiments, the lead is made using a biocompatible material. In at least some instances, the lead may be in contact with body tissue for extended periods of time. In some embodiments, the lead is made of material that is rigid until implanted and then becomes non-rigid. In other embodiments, only a portion of the lead (for example, the portion near a tip of the lead) is made of such material. The remainder of the lead can be formed of, for example, flexible or non-rigid material. The rigid portion facilitates the insertion of the lead.

The lead often has a cross-sectional diameter of no more than 1.5 mm and may be in the range of 1 to 1.2 mm. The lead often has a length of at least 10 cm and the length of the lead may be in the range of 30 to 70 cm. The length and cross-sectional diameter may depend on the application for which the lead is used.

Conductors (e.g., wires) 220 that attach to or form the electrode(s) 204 also pass through the lead 202. These conductors may pass through the material of the lead or through a lumen defined by the lead. The conductors are presented at the connector 208 (or at the control unit if no connector is present) for coupling of the electrode(s) 204 to the control unit 210. The control unit can provide stimulation signals, often in the form of pulses, to one or more stimulation electrodes. In addition, if there are one or more recording electrodes on the lead, the same or a different control unit can observe and record signals from the one or more recording electrodes.

The electrodes 204 can be made using a metal, alloy, conductive oxide, or other conductive material. Examples of suitable materials include platinum, iridium, platinum iridium alloy, stainless steel, titanium, or tungsten. Any type of electrode can be used including monopolar electrodes, bipolar electrodes, and other multipolar electrodes. A variety of shapes can be used for the electrodes including, for example, rings around the lead or electrodes in the form of circles, ovals, squares, rectangles, triangles, etc disposed on the surface of the lead.

In some embodiments, two or more different types of electrodes can be provided including, for example, recording electrodes and stimulation electrodes. Examples of deep brain stimulation leads that include multiple electrodes are provided in U.S. patent application Ser. No. 11/030,546, incorporated herein by reference. Recording electrodes can be used, for example, to monitor insertion of the lead and determine where the tissue to be stimulated is located. Subsequently, the stimulation electrodes can be used to stimulate the tissue. In some embodiments, the stimulation electrodes can also function as recording electrodes.

In one example of a method of using the lead 202, access to the desired position in the body can be accomplished by opening a hole through the patient's skin. The point of entry, as well as whether a hole is made in other tissues prior to inserting the lead, will depend on the application. The lead 202, which is still rigid, can be inserted into the tissue. The lead can be guided to the target location within the body while it maintains sufficient rigidity. The optional recording electrode(s) can be observed using an external control unit to identify the target tissue, if desired. Once in place, the lead can be positioned and anchored. The lead then becomes non-rigid over time as it is exposed to the body tissue.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of treating body tissue, the method comprising:
    implanting a lead comprising a plurality of stimulating electrodes disposed on a lead body into the body tissue without bending the lead body during the implantation, wherein the lead body is rigid to prevent bending of the lead body throughout the implanting of the lead into the body tissue;
    making the lead body non-rigid after completing the implanting of the lead into the body tissue and upon exposure to the body tissue, wherein making the lead body non-rigid comprises raising a temperature of the lead body, wherein the lead body comprises a plastic material having a glass transition temperature near or below body temperature; and
    stimulating the body tissue using the stimulation electrodes.

2. A method of treating body tissue, the method comprising:
    lowering a temperature of a lead below room temperature prior to implanting the lead into the body tissue, wherein the lead comprises a plurality of stimulating electrodes disposed on a lead body;
    implanting the lead into the body tissue without bending the lea body during the implantation, wherein the lead body is rigid to prevent bending of the lead body throughout the implanting of the lead into the body tissue;
    making the lead body non-rigid after completing the implant of the lead into the body tissue and upon exposure to the body tissue; and
    stimulating the body tissue using the stimulation electrodes.

3. A device for stimulating tissue inside a patient's body, comprising:
    a lead body that is configured and arranged to be substantially rigid outside the patient's body and throughout a procedure for implantation of the lead into the patient's body and then becomes non-rigid after completing the implantation procedure and upon exposure within the patient's body, wherein the lead body is configured and arranged to maintain a same shape throughout implantation, wherein the lead body comprises a plastic material that has a glass transition temperature that is below room temperature; and
    a plurality of stimulating electrodes disposed on the lead body.

* * * * *